(12) United States Patent
Heikkilä et al.

(10) Patent No.: US 6,894,199 B2
(45) Date of Patent: May 17, 2005

(54) PROCESS FOR THE PRODUCTION OF XYLITOL

(75) Inventors: Heikki Heikkilä, Kantvik (FI); Heikki Ojamo, Kirkkonummi (FI); Matti Tylli, Kantvik (FI); Vili Ravanko, Clinton, IA (US); Juha Nurmi, Kirkkonummi (FI); Piia Haimi, Espoo (FI); Raimo Alen, Helsinki (FI); Hannu Koivikko, Kantvik (FI)

(73) Assignee: Danisco Sweeteners Oy, Espoo (FI)

( * ) Notice: Subject to any disclaimer, the term of this patent is extended or adjusted under 35 U.S.C. 154(b) by 0 days.

(21) Appl. No.: 10/134,910

(22) Filed: Apr. 29, 2002

(65) Prior Publication Data

US 2003/0097029 A1 May 22, 2003

Related U.S. Application Data

(60) Provisional application No. 60/287,222, filed on Apr. 27, 2001.

(51) Int. Cl.$^7$ .................... C07C 31/18; C07C 31/24; C07C 31/22; C07C 31/20

(52) U.S. Cl. ................ 568/864; 568/852; 568/861; 536/124; 536/127; 536/128; 435/94; 435/190; 435/158

(58) Field of Search ................ 568/864, 852, 568/861; 435/158, 190, 94; 536/124, 127, 128

(56) References Cited

U.S. PATENT DOCUMENTS

| | | | |
|---|---|---|---|
| 3,586,537 A | 6/1971 | Steiner et al. | |
| 3,784,408 A | 1/1974 | Jaffe et al. | |
| 4,008,285 A | 2/1977 | Melaja et al. | |
| 4,066,711 A | 1/1978 | Melaja et al. | |
| 4,075,406 A | 2/1978 | Melaja et al. | |
| 4,326,072 A | 4/1982 | Kruse et al. | |
| 4,631,129 A | 12/1986 | Heikkila et al. | |
| 5,081,026 A | 1/1992 | Rahkila et al. | |
| 5,096,820 A | 3/1992 | Leleu et al. | |
| 5,238,826 A | 8/1993 | Leleu et al. | |
| 5,563,303 A | * 10/1996 | Vuorinen | ............ 568/864 |
| 5,637,225 A | 6/1997 | Heikkila et al. | |
| 5,714,602 A | 2/1998 | Beck et al. | |
| 5,872,247 A | 2/1999 | Fleche et al. | |
| 5,998,607 A | * 12/1999 | Heikkila et al. | ............ 536/124 |

FOREIGN PATENT DOCUMENTS

| | | |
|---|---|---|
| FI | 102545 B | 12/1998 |
| FR | 2772788 | 6/1999 |
| JP | 5076379 | 3/1993 |
| WO | WO 91/15588 | 10/1991 |
| WO | WO 94/10325 | 5/1994 |
| WO | WO 0112834 A1 | 8/2000 |

OTHER PUBLICATIONS

Biochimie, vol. 58, 1976, Y.N. Karassevitch: "The Utilization of Rare and Unnatural Pentoses by Yeast Torulopsis Candida", pp. 239–242.

Agric. Biol. Chem., vol. 44, No. 6, 1980, Ken Izumori et al: Evolution of D–Arabinose, L–Xylose and L–Ribose Utilization in Mycobacterium Smegmatis: Mutants with a Novel Enzyme "Pentose Reductase", pp. 1443–1446.

STN International, File CAPLUS, CAPLUS accession no: 1960:110071, Document no: 54:110071, E. Dimant et al: "Preparation of L–Xylose"; J. Org. Chem. (1960), 25, 475–6.

Kobori, et al., "Substrate Specificity and Carbohydrate Synthesis Using Transketolase", J. Org. Chem. 1992, 57, pp. 5899–5907.

Bhuiyan, et al., "A New Method for the Production of L–Lyxose from Ribitol Using Microbial and Enzymatic Reactions", Journal of Fermentation and Bioengineering, vol. 86, No. 5, 513–516, 1998.

Moyroud, et al., "L–Ribonucleosides from L–Xylose", Tetrahedron 55, 1999, 1277–1284.

Roper, "Selective Oxidaton of D–Glucose: Chiral Intermediates for Industrial Utilization", starch/starke 42, 1990, Nr. 9, S. 342–349.

Isbell, "Preparation of Lower Aldonic Acids by Oxidation of Sugars in Alkaline Solution", Part of Journal of Research of the National Bureau of Standards, vol. 29, Sep. 1942.

Stein, et al., "Enzyme Evolution: A Promising Method for Obtaining New Enzymes for Carbohydrate Synthesis", Forum for Applied Biotechnology, 1995, Part 1, pp. 1911–1919.

Schmid, et al., "Chemo–Enzymatic Synthesis of Carbohydrates: The Preparation of L–Xylose and 2–Deoxy–L–Xylo–Hex se", Liebigs Ann. Chem. 1992, pp. 95–97.

Saito, et al., "Conversion of L–Ascorbic Acid to L–Idonic Acid, L–Idon–.Gamma.–Lactone and 2–Keto–L–Idonic Acid in Slices of Immature Grapes", Plant Cell Physiol. 1982, 23 (3), pp. 499–507.

Kanzaki, et al., "2–Keto–L–Gulonic Acid Fermentation. IV. L–Sorbose Metabolism in Pseudomonas Aeruginosa", Agr. Biol. Chem. (1970), 34 (3), 432–436.

Makover, et al., "New Mechanisms for the Biosynthesis and Metabolism of 2–Keto–L–Gulonic Acid in Bacteria", Biotechnol. Bioeng. (1975), 17(10), 1485–1514.

Fioshin, et al., "Electrosynthesis of Physiologically–Active Compounds", Vses. Soveshch. Elektrokhim., 5th (1975), vol. 1, pp. 339–342, 1974.

* cited by examiner

Primary Examiner—Elvis O. Price
(74) Attorney, Agent, or Firm—Scully, Scott, Murphy & Presser (57) ABSTRACT

The present invention relates to the production of xylitol. In particular, processes utilising L-xylose as an intermediate for xylitol production are described. The present invention also relates to process for the preparation or L-xylose, as an intermediate, by-product or end-product to be used per se.

14 Claims, 1 Drawing Sheet

Figure 1

PROCESS FOR THE PRODUCTION OF XYLITOL

RELATED APPLICATION

This application claims benefit of U.S. Provisional Application Ser. No. 60/287,222, filed on Apr. 27, 2001.

FIELD OF THE INVENTION

The present invention relates to the production of xylitol. In particular, the invention relates to processes for the production of xylitol through routes utilizing L-xylose as intermediate.

BACKGROUND OF THE INVENTION

Xylitol is a naturally occurring 5-carbon sugar alcohol, which is present in small amount in many fruits and vegetables and is produced in the human body during normal metabolism. It has approximately the same sweetness as sucrose, lower caloric content of about 2.4 kcal/g, and it has certain known metabolic, dental and technical characteristics which make it an attractive special sweetener or sugar substitute in various contexts. For instance, xylitol is cariostatic and even anti-cariogenic. It is metabolised independently of insulin and can be safely consumed by non-insulin dependent diabetics, and it is non-toxic. Nowadays it is widely used in chewing gums, dental care products, health promoting products, functional food products, pharmaceutical products, confectionery products and the like.

Xylitol is usually prepared by processes utilizing natural raw materials, especially xylan-containing materials. In current use are methods in which a xylan-containing material is first hydrolysed to produce a mixture of monosaccharides, including D-xylose. After purification, the D-xylose is then converted to xylitol, generally in a chemical process using e.g. a nickel catalyst such as Raney-nickel. A number of processes of this type have been described in the literature of the art. U.S. Pat. No. 3,784,408 (Jaffe et al.), U.S. Pat. No. 4,066,711 (Melaja et al.), U.S. Pat. No. 4,075,406 (Melaja et al.), U.S. Pat. No. 4,008,285 (Melaja et al.) and U.S. Pat. No. 3,586,537 (Steiner et al.) may be mentioned as examples.

The recovery of D-xylose during wood and pulp processing can be performed by various separation techniques. Chromatography is widely used. A process for the fractionation of sulfite spent liquor by chromatography is described in U.S. Pat. No. 5,737,225, Xyrofin Oy. The process uses a simulated moving bed including at least two chromatographic beds and, preferably, at least three different fractions are recovered, one of these being enriched with xylose and another with lignosulphonates. For instance U.S. Pat. Nos. 4,631,129; 4,008,285 and 4,075,406 also describe chromatographic processes for the recovery of xylose.

Processes in which microorganisms are utilised for biotechnological production of xylitol have also been described. It is known that many yeast strains produce reductase enzymes that catalyse the reduction of sugars to corresponding sugar alcohols. Many yeasts, in particular *Pichia, Candida, Hansenula* and *Kluyveromyces*, are also capable of reducing xylose to xylitol as an initial step in their xylose metabolism.

The reaction route or pathway of xylose utilisation for yeasts is in general the following: xylitol is synthesised in the first step by reduction of xylose to xylitol with the aid of xylose reductase. Xylitol is then metabolised by a series of successive steps. Xylitol is first oxidised to xylulose with xylitol dehydrogenase, xylulose is phosphorylated to xylulose-5-phosphate with xylulose kinase (also called xylulokinase), and then part of the xylulose-5-phosphate is converted to pyruvate via several intermediate steps. Also ethanol and $CO_2$ can be formed. The reactions are not tightly coupled, and the relevant main products and by-products vary depending on the yeast strain and the fermentation conditions, such as oxygen availability.

For instance PCT publications WO 90/8193, WO 91/0740, WO 88/5467 and French published application 2 641 545 describe the use of *Candida tropicalis, Candida guilliermondii* and *Candida parapsilosis*, respectively, for the industrial production of xylitol.

U.S. Pat. No. 5,081,026, Heikkilä et al., describes a process for the production of xylitol from xylose, in which an aqueous xylose solution is fermented with a yeast strain capable of converting free xylose to xylitol and free hexoses to ethanol. After fermentation, a xylitol-rich fraction is obtained by chromatographic separation, and finally, xylitol is recovered from said fraction.

Genetic modification of microorganisms in order to enhance their xylitol production have also been reported in the literature of the art. For examples, in WO 91/15588, Hallborn, J. et al. describe the cloning of the xylose reductase gene from *Pichia stipitis* into *Saccharomyces cerevisiae*. Gong C. et al., *Biotechnol. Letters* 3:125–130 (1981) describe two high xylitol producing yeast mutants denominated HXP 1 and HXP 2, obtained after UV-mutagenesis of a wild strain of *Candida tropicalis* which originally was capable of metabolising D-xylose into xylitol.

EP 0 604 429, Xyrofin, describes novel yeast strains with modified xylitol metabolism, a process for the production of said strains, and the use of said strains in a process for producing xylitol. The strains are capable of reducing xylose into xylitol, but are deficient in one or more enzymes involved in the xylitol metabolism, with the effect that the xylitol produced accumulates in the culture medium and can be recovered therefrom. The yeasts described belong to the genera *Candida, Hansenula, Kluyveromyces* or *Pichia*, and the genetic modification eliminates or reduces expression of the gene that encodes xylitol dehydrogenase or xylulose kinase, or both.

Another approach that has been suggested for the bioproduction of xylitol is the enhancement of xylose production, thus providing more xylose as the primary metabolite for xylitol production.

Some fungi, including *Aureobasidium, Aspergillus, Trichoderma, Fusarium* and *Penicillium*, have been reported to have xylanolytic activity and thus be able to degrade xylan-containing biopolymers into xylose. E.g. Kuhad R. C. et al., *Process Biochemistry* 33:641–647 (1998) describe a hyperxy-lanolytic mutant strain of *Fusarium oxysporum* produced by UV and N-methyl-N'-nitro-N-nitrosoguanidine (NTG) treatment.

EP 0 672 161, Xyrofin, describes a method for the production of xylitol from carbon sources other than xylose and xylulose by using recombinant hosts. The microorganisms produce xylitol via an altered arabitol route involving in particular arabitol dehydrogenase, and/or via altered (over)expression of genes encoding the enzymes of the oxidative branch of the pentose phosphate pathway (PPP), in particular glucose-6-phosphate dehydrogenase or 6-phospho-D-gluconate dehydrogenase, thus enabling utilisation of glucose, for instance. When used, D-glucose is phosphorylated into D-glucose-6-phosphate and converted to D-ribulose-5-phosphate via 6-phospho-D-gluconate. The D-ribulose-5-phosphate is then epimerised to D-xylulose-5- phosphate, dephosphorylated to D-xylulose and reduced to xylitol. Amplification of glucose-6-phosphate dehydrogenase enzyme activity in osmotolerant yeasts is also described in FR 2 772 788, Roquette Freres.

U.S. Pat. No. 5,096;820, Leleu et al., also describes a process in which xylitol is produced from D-glucose. Glucose is first microbiologically converted to D-arabitol, which likewise is microbiologically converted to D-xylulose. The D-xylulose is then enzymatically isomerised into a mixture of D-xylose and D-xylulose, which is catalytically hydrogenated. Finally, the xylitol is recovered by chromatographic separation or crystallisation. The D-arabitol containing fractions, or the mother liquor from crystallization, which are rich in xylitol but also in D-arabitol, are preferably recirculated into the process. U.S. Pat. No. 5,238,826, Leleu et al., uses a similar process to obtain D-xylose, ultimately for the preparation of xylitol by hydrogenation. Also in this process, D-glucose is first microbiologically converted to D-arabitol, which then likewise is microbiologically converted to D-xylulose. The D-xylulose is then enzymatically isomerised into a mixture of D-xylose and D-xylulose. Finally, the mixture is subjected to chromatographic separation, the D-xylose fraction is recovered, and the D-xylulose fraction is recirculated into the isomerisation step.

The background art thus describes the production of xylitol from naturally occurring raw materials. At present, the raw materials mainly used are xylan-containing materials. From xylan, xylitol is produced by chemical processes or combinations of chemical and biological processes. Further, processes utilising microorganisms, in particular yeasts, capable of producing xylitol from monosaccharide solutions or pure D-xylose solutions have been described. Generally, the xylose found in nature, and hence in natural raw materials, is the D-isomer. Also the xylitol and xylose metabolism in microorganisms seems to involve the D-isomer.

In view of the increasing use of xylitol, in particular in health promoting products, functional foods, dental care products, and in the confectionary industry, new methods for the production of xylitol would be welcome. In particular, there is an expressed need for processes for the production of xylitol from other sources than those previously utilised.

U.S. Pat. No. 5,714,602, Cerestar Holding B. V., discloses a process developed from this viewpoint. According to the document, xylitol is produced from gluconic acid. In a first step, gluconic acid is decarboxylated, by using sodium-hypochlorite or hydrogen peroxide into arabinose, which through hydrogenation is converted into arabinitol. After isomerisation, a mixture of xylitol, ribitol and D,L-arabinitol is obtained, from which xylitol is recovered by chromatographic methods.

EP 754 758, Cerestar Holding B. V., relates to a process for the production of xylitol in two steps. In the first step a hexose is converted to a pentitol by fermentation, and in the second step the pentitol is catalytically isomerised to yield a pentitol mixture. Specifically, the document describes a process in which glucose is fermented to arabinitol and then isomerised into a pentitol mixture containing xylitol, ribitol and D,L-arabinitol. Xylitol can be recovered from said mixture by chromatographic methods.

WO 93/1903, Amylum, also describes a process for the production of xylitol from monosaccharides, in particular D-glucose, D-fructose, D-galactose, L-sorbose or mixtures thereof. The starting material is first oxidised to D-arabinonic acid, D-lyxonic acid, and/or L-xylonic acid, and the intermediate is then hydrogenated in one or several steps to a product consisting mainly of xylitol or a mixture of xylitol, arabinitol and ribitol. Finally, if necessary, xylitol is separated by means of chromatography.

SHORT DESCRIPTION OF THE INVENTION

The present invention takes advantage of the fact that xylitol does not exist in D- or L-form, and thus can be prepared both from D- and L-monosaccharides and derivatives thereof. As outlined above, previously mainly the D-forms, in particular D-xylose, have been used.

The present invention is based on the utilisation of L-xylose as an intermediate in xylitol production.

The present invention also relates to processes for preparing pentoses from hexoses or derivates thereof, or pentitols. In particular, L-pentoses are prepared.

It is thus an object of the present invention to provide a process for the preparation of xylitol by utilising purified L-xylose as intermediate.

It is also an object of the present invention to provide a process for the preparation of crystalline xylitol by utilising L-xylose as intermediate.

It is further an object of the present invention to provide processes for the preparation of L-xylose, as an intermediate, or as a by-product or end-product to be used per se.

In a preferred embodiment of the invention, L-xylose is prepared from a 6-carbon monosaccharide or a derivative thereof by a two-step process comprising reduction and decarboxylation.

In another preferred embodiment, the intermediates for L-xylose are prepared by fermentation.

It is also an object of the present invention to provide processes for the preparation of L-monosaccarides and derivates thereof, as well as L-hydroxy acids. In particular, L-xylulose, L-xylonic acid, L-idonic acid and L-gulonic acid are prepared and can be recovered, in part or totally, for other purposes than L-xylose and xylitol production.

DETAILED DESCRIPTION OF THE INVENTION

L-xylose is not a naturally occurring compound. It can be scarcely found in bacterial cell membranes, but does not otherwise seem to be found in nature.

The production of L-xylose from 2-hydroxyaldehyde through tran-sketolase-catalyzed condensation of hydroxy-pyruvic acid with said aldehydes have been described by Yoshihiro et al. Journal of Organic Chemistry 57 (1992) 22, pp. 5899–5907. Schmid et al. describe a synthetic approach to produce L-xylose by using a complex multistep procedure involving condensation of 3-phenylthio-propanal with dihydroxyacetone phosphate as the first step [Liebigs Ann Chem 0 (1992) pp. 95–97]. Patent publication CS 275890, Chemicky Ustav SAV, describes the production of L-ribose by epimerisation of L-arabinose, which as an intermediate product gives a mixture of L-ribose, L-arabinose, L-lyxose and L-xylose. Shakhawat et al. Journal of Fermentation and Bioengineering 86 (1998) 5, pp-513–516, describe the preparation of L-lyxose from ribitol by a microbial oxidation reaction, which yields L-xylulose as an intermediate. None of these processes are suitable for commercial use.

L-xylose is commercially available from Fluka under Chemical Abstract Registry Number CAS-No. 609-06-03.

Nucleoside analogues having unnatural β-L-configuration have lately proved to be inhibitors of viral proliferation. The L-isomer of xylose has a structurally close resemblance with D-ribose, the natural sugar constituent in nucleosides and nucleotides, and L-xylose has thus been suggested for use in drugs, in particular in antiviral drugs, both per se and in the preparation and study of other L-isomers of both known and unknown nucleosides. For example, Moyroud et al. describe in Tetrahedron 55 (1999) 5, pp. 1277–1284, conversion of L-xylose into a L-ribose derivative via an oxidation/reduction procedure. The L-ribosyl donor was submitted to a glycosidation reaction to give L-ribonucleosides, L-uridine, L-cytidine, L-adenosine and L-guanosine.

In connection with the present invention, several different routes for the preparation of L-xylose have been developed. The preparation processes involve multi-step methods based mainly on decarboxylation, reduction and isomerisation reactions performed on a number of chosen monosaccharides and derivatives thereof. The inter-molecular reactions are performed in appropriate order.

The reaction will depend on the type of starting compound. Sugar chains are relatively easily degraded, and keto forms are usually less stable than corresponding molecules containing an aldehyde group. Aldonic acids and uronic acids are predominantly in lactone ring form, and the lactones, especially the major 1,4-lactones, are relatively stable molecules. However, the aldonic acid lactones are more susceptible to hydrogenation reactions than linear chain forms, such as the corresponding salts.

The L-xylose prepared is separated and purified. In purified form, it can be used as an end product, for instance for the purposes outlined above.

The prepared and purified L-xylose can also be utilised for the production of xylitol.

In accordance with the present invention, hydroxy acids have been found to be useful as raw materials. In particular, ketoalduronic acids, aldonic acids and uronic acids are found useful. Specific examples of such preferred starting materials include, but are not limited to glucuronic acid, gulonic acid, idonic acid, ketogluconic acids, ketogulonic acids and xylonic acid.

2-keto-L-gulonic acid is one of the preferred hydroxy acids. The 6-carbon 2-keto-L-gulonic acid can be decarboxylated to L-xylonic acid. L-xylonic acid is in turn hydrogenated into L-xylose, which is converted into xylitol through a reduction reaction. Alternatively, 2-keto-L-gulonic acid can be decarboxylated into L-xylulose, which then is isomerised to L-xylose. Enzymatic or chemical reduction of 2-keto-L-gulonic acid, on the other hand, will result in L-gulonic acid or L-idonic acid, or a mixture of said epimers, which compounds are decarboxylated into the 5-carbon L-xylose, and finally converted into xylitol.

2-keto-L-gulonic acid is produced e.g. as a by-product in the preparation of vitamin C, and is commercially available. 2-keto-L-gulonic acid can also be obtained by microbiological fermentation of sorbose via sorbosone.

D-glucuronic acid can also be utilised for the reaction. Reduction of D-glucuronic acid yields L-gulonic acid, which can be decarboxylated into L-xylose as described above.

D-glucuronic acid is commercially available.

Also L-xylonic acid can be generated through different routes, for instance by decarboxylation of L-sorbose, a ketohexose.

L-sorbose is commercially available. It is produced e.g. as a by-product in the preparation of vitamin C.

It is also known that even L-ascorbic acid (vitamin C) can be reduced back to L-gulonic acid (Paul Ryvander, Hydrogenation methods, Academic Press 1985, p. 66).

Alternatively, fermentation can be used. This will enable the utilisation of a large scale of starting materials. For example, L-idonic acid is formed during fermentation of e.g. D-glucose, D-sorbitol, L-sorbose or 5-keto-D-gluconic acid, and can be decarboxylated into L-xylose and eventually reduced to xylitol. For instance the following processes may be used: from D-glucose by *Erwinia herbicola* (Lazarus, R. A., Seymour, J. L. Stafford, R. K. Dennis, M. S., Lazarus, M. G., Marks, C. B., Anderson, S. in Biocatalysis (Ed. Abramovicz, D. A.) pp. 135–155. van Nostrand Rheinhold, New York 1990); from L-sorbose and D-sorbitol by *Gluconobacter melanogenus* (Sugisawa, T., Hoshino, T., Masuda, S., Nomura, S., Setoguchi Y., Tazoe, M., Shinjoh, M., Someha, S., Fujiwara, A. Agric Biol. Chem. 54(1990) 1201–9); from D-sorbose by *Pseudomonas putida* (Makeover, S., Ramsey, G. B., Vane, F. M., Witt, C. G., Wright, R. B. Biotechnol. Bioeng. 17(1975) 1485–1514), and from 5-keto-D-gluconic acid by *Brevibacterium* (Sonoyama, T., Kageyama, B., Honjo, T., JP 74125589 (1974). Other possibilities include for instance the preparation of L-xylulose by fermentation of e.g. xylitol, which xylulose is then further processed as outlined above. Preparation of 5-keto-D-gluconic acid has been described by R öper, Starch/Stärke 429, (1990) 342–349.

Consequently, in addition to the hydroxy acids mentioned above, also specific 6-carbon monosaccharides and their corresponding sugar alcohols, such as glucose, sorbose and sorbitol, are regarded as preferable raw materials. Generally, the D-form monosaccarides are prevalent in nature. However, L-arabinose and L-rhamnose are naturally occuring compounds.

Examples of specific methods for performing the reactions can be found in the literature of the art. A plentitude of suitable catalysts, reduction agents, oxidation agents, enzymes, further reagents and reactions conditions have been described. Procedures, by which the intermediate and final procucts could be recovered and purified, have, however, not been described with sufficient clarity to enable production of industrially applicable products.

Decarboxylation reactions can be effected by hydrogen peroxide or hypochlorite, for instance. A suitable method is the so-called Ruff reaction, utilising a combination of hydrogen peroxide and ferrous sulphate as reduction agent [see e.g. Ruff, Berichte der Deutschen Chemischen Gesellschaft 32 (1899) 553–554, and E. Fischer, O. Ruff, Ber. 33 (1900) 2142]. Reduction can be carried out chemically, for instance by catalytic hydrogenation, or enzymatically.

Decarboxylation of 2-ketoaldonic acids has been described by Matsui, M, Uchiyama, M. and Liau, Agr. Biol. Chem. 27(1963) 3, p. 180–184. The authors present a scheme for the decarboxylation of 2- and 3-ketoacids into corresponding ketoses and aldoses, and elaborate on the importance of a metall ion catalyst. Nickel ion catalyzed decarboxylation of 2-keto-D-gluconic acid in pyridine yielded D-ribulose as the main product. In addition, D-arabinose was found in a smaller amount. Decarboxylation of 2-keto-L-gulonic acid, on the other hand, yielded L-xylose and L-xylulose in approximately equal amounts. It is mentioned that D-arabinose and L-xylose possibly are formed from the main products D-ribulose and L-xylulose due to an alkaline isomerisation process mediated by the pyridine used. An improved method avoiding both the use of pyridine which is harmful in itself, and the isomerisation process, is described in U.S. Pat. No. 5,872,247, Duflot, P. and Fleche, G. The nickel ion catalysed decarboxylation process is performed by putting an aqueous solution of 2-ketoaldonic acid in contact with a resin carrying vinylpyridine groups. According to the document, the process allows for obtaining the ketose of the corresponding functionality immediately lower than the aldonic acid in high yield and purity. D-ribulose is disclosed as the decarboxylation product of 2-keto-D-gluconic acid, D-xylulose of 2-keto-D-galactonic acid, and D-erythrulose of 2-keto-D-arabinonic acid, respectively.

Hydrogenation of 5-keto-D-gluconic acid to L-idonic acid and D-gluconic acid has been described by Caldeira et al., Neth. Recl. Trav. Chim. Pays-Bas 110 (1991)4, pp. 111–114. In particular, the authors report on the influence of the choice of catalyst and the presence of other additives on the selectivity of the reaction. With palladium boride as the best catalyst, the conversion was almost 100% and the molar ratio between L-idonic acid and D-gluconic acid about 3:1. Hydrogenation of D-glucuronic acid is described in U.S. Pat. No. 4,326,072, Kruse et al., ICl. The hydrogenation is carried out in a solvent, preferably an aqueous solution, and utilises a ruthenium metal catalyst, preferably on a solid support. The hydrogenation is effected at elevated temperatures, in particular about 80–120° C. According to the document, the reaction will be too slow at lower temperatures, and in higher temperatures, the incidence of by-products will increase. In the conditions mentioned above, hydro-generation of D-glucuronic acid results in colourless and relatively pure L-gulonic acid. In contrast, hydrogenation of D-glucuronic acid using a nickel catalyst requires higher temperatures of about 140–150° C. and will nevertheless, according to the document, result in dark brown L-gulonic acid and high yields of pentoses and tetroses as undesired by-products.

L-xylonic acid has been prepared from L-sorbose. For example, Isbell et al., J. Res. Nat. Bur. Stand. 29 (1942) 227–232, used oxygenation of L-sorbose, in conditions comprising an oxygen pressure of about 0.1 MPa at room temperature, to obtain a yield of about 42.6 mol % L-xylonic acid. Berezojskij and Strelchunas, J. Gen. Chem, U.S.S.R. 24 (1954) 855–858, effected a corresponding oxygenation reaction at a temperature of about 30–35° C. and about 3–3.5 MPa O2, and obtained a yield of 22% L-xylonic acid.

In a preferred embodiment, xylitol is produced from L-xylose obtained from a 6-carbon monosaccharide or a derivative thereof by a process comprising decarboxylation and reduction.

In connection with the present invention, decarboxylation means any reaction, in which the carbon chain of a sugar or a sugar derivative molecule is shortened by one carbon atom. Such reactions include, for instance, conversion of 2-ketoaldonic acids to one carbon atom shorter aldonic acids; of ketoses to one carbon atom shorter aldonic acids; and of aldonic acids to one carbon shorter ketoses or aldoses.

Preferably, L-gulonic acid, L-idonic acid, or L-xylonic acid is an intermediate. L-gulonic acid and its epimer L-idonic acid are often both present in reaction mixtures. L-gulonic acid can thus be used partly or totally in the form of L-idonic acid, and vice versa, and mixtures of L-gulonic acid and L-idonic acid in any proportions can be equally useful.

In one preferred embodiment of the present invention a mixture of L-idonic acid and D-gluconic acid is prepared by reduction of 5-keto-D-gluconic acid. Decarboxylation of said mixtures yields a mixture of L-xylose and D-arabinose, which can be separated from each other by chromatographic means, for instance.

In a particular embodiment of the present invention L-gulonic acid is prepared by reduction of D-glucuronic acid and subsequently decarboxylated into L-xylose. In another particular embodiment, L-gulonic acid, in addition to L-idonic acid, is prepared by reduction of 2-keto-L-gulonic acid, and then subsequently decarboxylated into L-xylose. L-idonic acid can also be prepared by fermentation, for instance of D-glucose or 5-keto-D-gluconic acid.

Another particular embodiment of the invention involves the utilisation of L-xylonic acid for the preparation of L-xylose and xylitol. L-xylonic acid is prepared by decarboxylation of 2-keto-L-gulonic acid and then in a reduction reaction converted to L-xylose. Alternatively, L-xylonic acid is prepared by decarboxylation, performed as degradation by alkali oxydation, of sorbose, and subsequently hydrogenated into L-xylose.

A further preferred embodiment of the present invention involves the preparation of xylitol from L-xylulose. L-xylulose is prepared from 2-keto-L-gulonic acid by decarboxylation and then isomerised to L-xylose. The isomerisation can be enzymatically performed. Appropriate enzymes having L-xyloseisomerase activity can be used for this purpose. L-xylulose can also be prepared by fermentation. For instance, galacto-oxidase producing microorganisms, such as *Panthoea ananatis, Alcaligenes* sp., *Rhodobacter sphaeroides, Erwinia uredovora*, can be used for the conversion of xylitol into L-xylulose. A mutant of *Rhodobacter sphaeroides* Si4, designated *Rhodobacter sphaeroides* D, possessing a galactitol dehydrogenase having a broad substrate specificity and being capable of producing e.g. L-xylulose from xylitol, has been described by Stein et al. Meded. -Fac. Landbouwkd. Toegepaste Biol. Wet. (Univ. Gent), 1995, 60 (4a, Forum for Applied Biotechnology, 1995, Part 1) 1911–19. Patent publication JP 5076379, Hayashibara Biochem Lab, Japan, describes the production of L-xylulose from xylitol by using *Alcaligenes denitrificans* subsp. *xylooxydans* 701A, FERM BP-2735. Doten et al. describe in Journal of Bacteriology 162 (1985) 2, pp. 845–848, four different microorganisms having inducible xylitol dehydrogenase activity. Only one, *Erwinia* 4D2P, was found to have a xylitol dehydrogenase enzyme catalysing the oxidation of xylitol into L-xylulose. In Applied and Environmental Microbiology 49 (1985) pp. 158–162, Doten et al. describe mutants of *E. urodovora* which constitutively synthesized xylitol-4-dehydrogenase activity, oxidizing xylitol to L-xylulose, and L-xylulokinase activity. One mutant, *Erwinia uredovora* DM122, had xylitol-4-dehydrogenase activity but lacked L-xylulokinase activity, and was thus regarded suitable for the production of L-xylulose from xylitol. The isomerisation reaction of L-xylulose to L-xylose can also be effected by using alkali, such as NaOH. Alkaline isomerisation has been described by de Bruijn et al., Sugar Technology Reviews 13 (1986) 21–52.

In accordance with the present invention, the following processes are regarded as particularly preferred. As a final step, xylitol can be recovered.

1. 2-keto-L-gulonic acid is decarboxylated into L-xylonic acid, which is reduced to L-xylose and xylitol. The final products are separated and crystallized. The first reaction is easily accomplished due to the reactive keto group in the starting material. The xylonic acid obtained, on the other hand, is much more stable and therefore it is necessary to improve the reaction rate e.g. by using catalysts such as ruthenium or nickel catalysts. Ru/C in methanol is regarded as preferred.

2. 2-keto-L-gulonic acid is reduced into a mixture of L-gulonic and L-idonic acid. The reduction can be accomplished e.g. by hydrogenation while protecting the carbonyl group by formation of an appropriate salt, and the acids are then decarboxylated to L-xylose. The decarboxylation is preferably carried out as a Ruff reaction using hydrogen peroxide and ferrous sulphate.

3. D-glucuronic acid is reduced to L-gulonic acid, which subsequently is decarboxylated in a Ruff reaction into L-xylose. The starting material D-glucuronic acid can be prepared for instance from cellulose or starch by oxidation at the 6-carbon and by hydrolyzing the polyglucuronate. The reduction reaction is preferably carried out on D-glucuronate, thus effecting reduction of the aldehyde group.

4. L-sorbose is decarboxylated into L-xylonic acid, for instance with hydrogen peroxide. The reaction can be enhanced by using anthraquinone-sulphonate as oxidation agent and by adding alcohol to the reaction medium. The L-xylonic acid is then reduced, e.g. by hydrogenation using ruthenium carbon as catalyst, to L-xylose and/or xylitol.

5. 2-keto-L-gulonic acid is decarboxylated into L-xylulose, which then is isomerized, to L-xylose. The latter reaction can be performed enzymatically, microbiologically, or with alkali. The L-xylulose can also be recovered and circulated into the isomerisation step. L-xylose is recovered and possible reduced to xylitol.

6. Xylitol is oxidized at the 4-carbon to L-xylulose. The oxidation is preferably effected by microbes, in particular *Pantoea ananatis*. After separation of the cell mass, said L-xylulose is isomerised by L-xylose isomerase to L-xylose. L-xylulose, L-xylose and xylitol are separated. When desired, L-xylulose is recovered and the xylitol possibly recirculated. Also L-xylose can be recovered and reduced to xylitol: The final step usually involves crystallisation of the final end product and drying of the crystals. In some cases, where xylitol inhibits the enzymatic isomerisation process, it may be appropriate to include a separation step before said enzymatic isomerisation. The oxidation reaction can be carried out using any suitable galactose oxidase producing microorganism, such as those mentioned above. The separation processes are usually performed by chromatography.

7. L-idonic acid is produced by fermentation of D-glucose, D-sorbitol, L-sorbose, or 5-keto-D-gluconic acid. The L-idonic acid obtained is separated from the fermentation broth and purified, if desired. Thereafter, L-idonic acid is decarboxylated in a Ruff reaction into L-xylose, which finally is hydrogenated to xylitol.

8. 5-keto-D-gluconic acid is hydrogenated into a mixture of L-idonic acid and D-gluconic acid. Said mixture is decarboxylated to a mixture of L-xylose and D-arabinose, which are chromatographically separated from each other.

After purification, L-xylose can be converted into xylitol by chemical, enzymatical or microbiological reduction. Chemical reduction, by using e.g. hydrogenation, boron hydride, amalgam, or electrochemical reduction, is regarded as preferred. Most preferably, catalytic hydrogenation is used. Microbiological reduction of L-xylose into xylitol by *Torulopsis candida* has been described e.g. by Karassevitch, Y. N. Biochimie Paris 58 (1976) pp. 239–242.

L-xylose can also be separated, purified and even crystallized for use as an intermediate, for xylitol production, but also for use as such, for instance as an active agent in anti-viral drugs, or for the preparation of other non-naturally occurring L-analogues.

In a corresponding manner, the invention also provides for the separation and recovery of the other intermediates prepared by using the reaction steps outlined above.

In general, the compounds are in the L-form, which is less common in nature.

Processes suitable for recovery and purification of the products have been described in the literature of the art. Separation and purifications techniques such as chromatography, ion exchange, and membrane processes, e.g. ultrafiltration, nanofiltration, and electrodialysis, may be mentioned by way of example. In order to obtain a highly pure product, crystallisation can be used. Separation and crystallisation of xylitol has been described e.g. in U.S. Pat. No. 4,066,711, Melaja et al.

The purity of the product is an important feature of the invention. As described in the examples, xylitol can be obtained in a purity of over about 95%, for instance about 98.5% and in particular about 99%. Similarly, the purity of L-xylose can be over about 90%, for instance about 98.5%, and in particular about 99%. For compounds which can exist both in L- and D-form, the correct chirality is also of great importance. With the process according to the present invention, correct chirality can be guaranteed. The compounds prepared contain less than 0.3% D-form as impurity (detection limit with gas chromatography).

The invention will be described in detail in the following specific examples. The examples are included herein for illustrative purposes only and are not to be construed as limiting or restricting the scope of the invention in any way.

EXAMPLE 1

Decarboxylation of 2-keto-L-gulonic Acid to L-xylonic Acid

Decarboxylation was effected with hydrogen peroxide in alkaline conditions and at room temperature as described by Isbell et al. Carbohydr. Res. 36 (1974) 283–291. For 2 mol of starting material, 6.25 mmol NaOH, 1–2 mol hydrogen peroxide and 600 mol water were used. After a reaction time of 17 h a yield of 1.139 mol L-xylonic acid per 2 mol of dry starting material was obtained.

EXAMPLE 2

Reduction of L-xylonic Acid to L-xylose and Xylitol

One molar (1 M) xylonic acid was reduced partly to xylose and xylitol by hydrogenating the acid using ruthenium catalyst as a catalyst. The conditions were: temperature 45° C., pressure 50 bar, reaction time 18 hours and the catalyst load 0.332 g of Ru/C (solids 49.4%) per 10 ml of 1 M xylonic acid solution. After the reaction the concentration of xylose was 0.2 g/100 ml, and of xylitol 14 g/100 ml.

EXAMPLE 3

Reduction of 2-keto-L-gulonic Acid to L-gulonic Acid and L-idonic Acid

Neutralised solution (1 M) of 2-keto-L-gulonic acid was hydrogenated to L-idonic- and L-gulonic acids using Raney-nickel as a catalyst. The conditions were: temperature 110° C., pressure 50 bar, catalyst load was 0.275 g of catalyst slurry per 10 ml solution. Reaction time was three hours. The amount of acids produced was 17 g/100 ml.

EXAMPLE 4

Hydrogenation of 2-keto-L-gulonic Acid to L-gulonic Acid and L-idonic Acid

Twenty percent (200 g/l) solution of neutralised 2-keto-L-gulonic acid was hydrogenated to L-idonic and L-gulonic acids using Raney-nickel as a catalyst. The conditions were: temperature 110° C., pressure 50 bar, catalyst load was 10% of catalyst slurry per total dry substance and batch volume 3 liters. Reaction time was two hours. The concentration of acids at the end of reaction was 154 g/l.

EXAMPLE 5

Decarboxylation of L-gulonic and L-idonic Acids to L-xylose

A mixture of L-gulonic and L-idonic acids was decarboxylated at a temperature of 60° C. and a pH of 4.5–5.5 using sodium hypochlorite for oxydation. The reaction time needed was 30–60 minutes. The concentration of the acid mixture was 20 g/100 ml: The concentration of L-xylose after the reaction was 10 g/100 ml.

EXAMPLE 6

Decarboxylation of L-gulono-1,4-lactone to L-xylose

Decarboxylation of L-gulono-1,4-lactone was performed by using hydrogen peroxide as oxidation agent. By using 2.5 mol L-gulono-1,4-lactone, 0.03 mol $Fe_2(SO_4)_3$ as catalyst and 10 mol of hydrogen peroxide a yield of 0.457 g L-xylose per g starting material was obtained. The reaction time was 26 h, the pH about 6, and the reaction temperature about 65° C.

EXAMPLE 7

Reduction of D-glucuronic Acid to L-gulonic Acid

D-glucuronic acid was hydrogenated to L-gulonic acid using Raney-Nickel as a catalyst (ten percent wet catalyst per batch by substance). The temperature was 100° C., and pressure 40 bar. The acid was neutralized to a pH of about 5 before reaction. L-gulonic acid can be further decarboxylated to L-xylose as described in example 5 or 6.

EXAMPLE 8

Preparation of L-xylonic Acid by Oxidation of L-sorbose

A reaction vessel containing 5 g NaOH and 0.2 g sodium anthraquinone-2-sulphonate, AMS, Merck Co., in 150 ml of a solution of 80 mass-% of methanol in water, was kept at a temperature of 25° C. L-sorbose, Merck Co., (70 g/130 ml water) and NaOH (32 g/32 ml water) was added batchwise with 15 min intervals while mixing. Oxygen was added to the mixture and the reaction was continued for about 2 h. The major end product was L-xylonic acid, in addition, treonic acid, glyceric acid and glycolic acid were formed, as well as a large amount of formic acid.

The use of AMS as oxidation agent is not necessary but can be avoided by using higher oxygen pressure.

EXAMPLE 9

Fermentative Production of L-xylulose

*Pantoea ananatis* ATCC 43074 was cultivated in a fermentor on LBG-kanamycin medium (10 g/l tryptone, 5 g/l yeast extract, 5 g/l NaCl, 10 g/glucose, 100 mg/l kanamycin) under the following conditions:

temperature 37° C.
pH controlled at 6,5–7,5
dissolved oxygen >30% of saturated concentration
20% inoculum from an overnight shake-flask culture on the same medium.

When all the glucose, analyzed enzymatically by the Boehringer glucose kit was consumed (10–15 h), sterile xylitol was added to the fermentor to a concentration of 40 g/l. Cultivation was continued for 96 h at which time the fermentation broth contained 6,7 g L-xylulose. The broth was clarified by centrifugation and sterile filtration.

EXAMPLE 10

Chromatographic Purification of L-xylulose

The clarified broth from example 9 was concentrated by evaporation to a dry solids (DS) concentration of 20 g/100 g and used for L-xylulose purification by chromatographic separation. The separation was performed in a chromatographic separation column as a batch process. A strongly acid cation exchange resin in $Ca^{2+}$ form (Mitsubishi Diaion) was used as the stationary phase and pure ion exchanged water as eluent. The cross linkage degree of the resin was 6.0% and the average particle size 0.2 mm. Separation temperature was 65° C. The diameter of the column was 0.1 m and the resin bed height about 1.4 m. The chromatographic separation was performed as follows.

Step 1.

About 0.7 liters of feed solution (containing L-xylulose, xylitol and salts) was introduced to the top of the resin bed through a heat exchanger. Feed (DS) concentration was 21.3 g/100 g.

Step 2.

The feed was eluted downwards in the column by feeding ion exchanged eluent water to the top of the resin bed. The flow rate 50 ml/min.

Step 3.

The outflow of the column was monitored continuously by on-line refractive index and conductivity measurement device. When the feed was coming out, the whole outflow was collected in test tubes with 2 min intervals.

The concentration (refractive index), pH and conductivity of all samples were measured. Selected samples were then analyzed with HPLC ($Ca^{2+}$ from resin) for composition. L-xylulose rich fractions were combined and evaporated. The L-xylulose purity of the combined fraction was about 91% on DS and the L-xylulose recovery about 90%.

EXAMPLE 11

Alkaline Isomerization to of L-xylulose

The L-xylulose fraction from the chromatographic separation described in example 10 was used as a feed solution for an alkaline isomerization step. L-xylulose solution containing 90% L-xylulose on DS (DS content 200 g/l) and NaOH content being 0.05 N was kept 48 H at 40° C. in continuous agitation. After the reaction the solution was cooled to 20° C. and the pH of the solution was adjusted by 0.1 N HCl to 5.0. L-xylulose and L-xylose contents were analysed by HPLC to be 64 and 18% on DS, respectively.

After the reaction the solution was purified by ion exchange, as described in example 13, and L-xylose and L-xylulose were then separated by chromatography, as described in example 10.

EXAMPLE 12

Production of L-xylose From 5-keto-D-gluconic Acid

Hydrogenation of 5-keto-D-gluconic acid to D-gluconic- and L-idonic acids was performed under the following conditions: Hydrogen pressure was 40 bar, reaction temperature 100° C. pH of the feed was adjusted to 5 before reaction. Feed syrup concentration was 400 g/l. The catalyst was Raney-nickel and the catalyst load was 10% wet catalyst per feed dry substance. Decarboxylation of the obtained mixture of D-gluconic acid and L-idonic acid as described in examples 5 and 6 yields L-xylose and D-arabinose, which subsequently are separated by chromatography.

EXAMPLE 13

Purification of L-xylose Syrup by Demineralization Using ion Exchange Resins Purification of the decarboxylated mixture of idonic-gluconic-acid (=L-xylose syrup) was effected using ion exchange resins. The resins were strong acid cation exchange resin (Purolite C 150) and weak base anion exchange resin (Purolite A 104). Feed syrup concentration was 300 g/l, flow rate during the run one bed volume per hour and temperature 40° C. Most of the salt was removed. The purity of the L-xylose was 18.5% DS in the feed solution, and 58% in the product fraction.

EXAMPLE 14

Chromatographic Separation of L-xylose

The reaction mixture from previous decarboxylation processes was purified by applying chromatographic separation. Feed solution had a high content of salts and lower amounts of L-xylose, xylitol, arabinitol and other components.

The separation was performed in a chromatographic separation column (diameter 0.1 m) as a batch process. A strongly acid cation exchange resin in Na$^+$ form was used, the bed height was about 1.6 m. A feed size of about 260 g dry substance was used having a concentration of 35 g/100 ml. Separation temperature was 65° C. and flow rate 50 ml/min. The separation was performed as follows:

Step 1.

About 700 ml of filtered and pH adjusted (pH 6, adjustment with NaOH) feed solution was introduced to the top of the resin bed.

Step 2.

The feed solution was eluted downwards in the column by feeding ion exchanged water to the top of the resin bed. The eluent was also heated to 65° C. The flow rate was controlled by an outflow pump being 50 ml/min.

Step 3.

The outflow of the column was monitored continuously by on-line dry substance (refractive index) and conductivity measurement device. The outflow was collected in separate tubes in 2 min. interval.

Step 4.

The composition of the collected samples was analyzed with HPLC (Pb$^{++}$ resin) and selected tubes then combined for product fraction.

Figure 1:
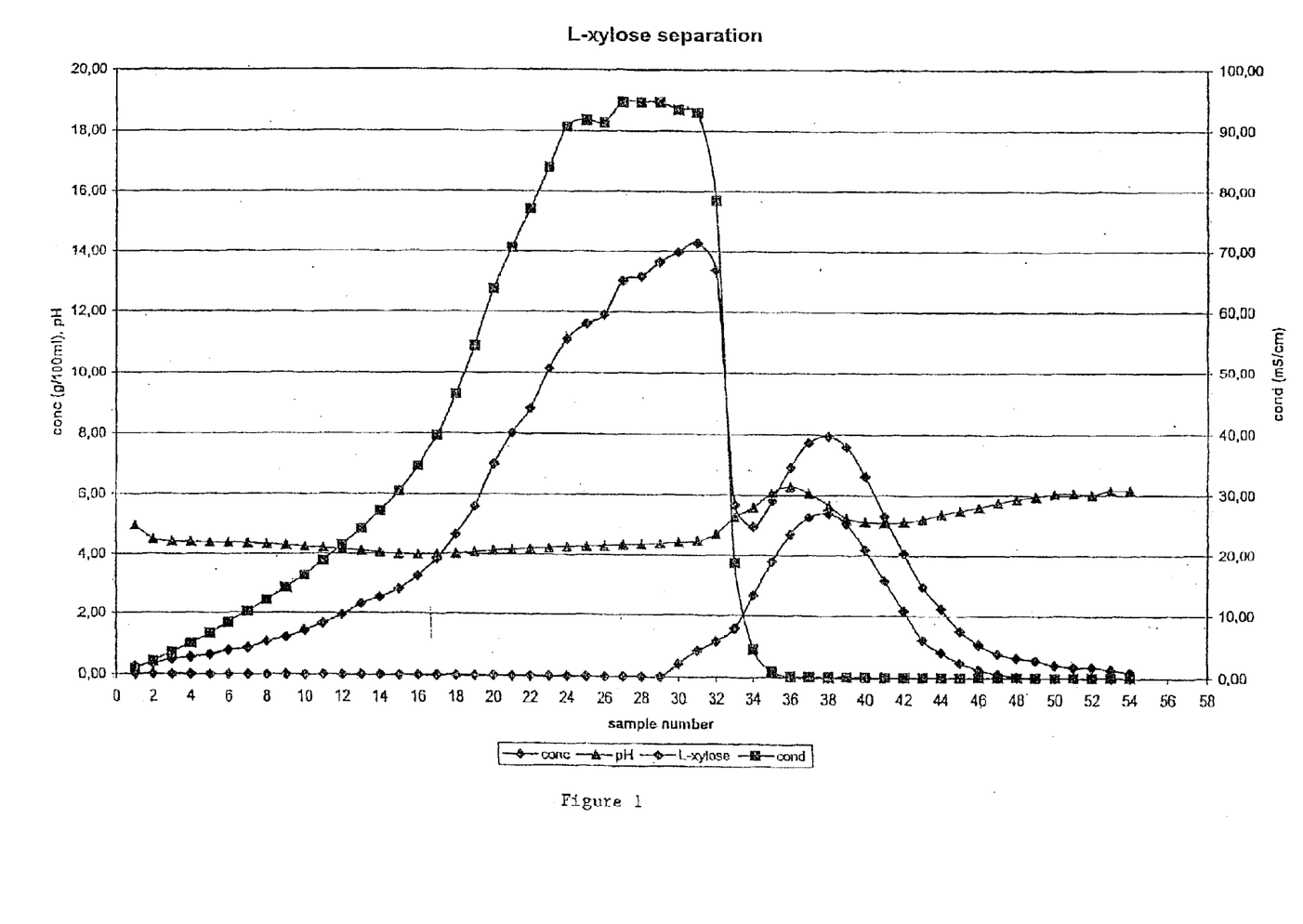
FIG. 1 shows chromatographic separation of L-xylose.

Table 1 presents composition of the feed solution and the outflow fraction. The separation profile is shown in FIG. 1. The yield is calculated by dividing the amount of L-xylose of the product fraction by the amount of L-xylose of all outcoming fractions.

TABLE 1

Composition of feed solution and outflow fractions

|  | Volume, l | DS, g/100 g | pH | Conductivity, mS/cm | L-xylose % % on DS | L-xylose yield, % |
| --- | --- | --- | --- | --- | --- | --- |
| Feed solution | 0.70 | 30.0 | 5.7 | 118 | 18.5 | — |
| Residual fraction 1 | 3.30 | 5.7 | 5.0 | 45 | 2.6 | 11.5 |
| Product fraction | 1.35 | 4.7 | 6.2 | 0.18 | 60 | 88 |
| Residual fraction 2 | 0.75 | 0.4 | 6.2 | 0.05 | 3.6 | 0.5 |

EXAMPLE 15

Chromatographic Separation of L-xylose and D-arabinose

Decarboxylation of a mixture of L-idonic acid and D-gluconic acid produced a mixture of L-xylose and D-arabinose, as major components, as described in example 12. The mixture was purified by applying chromatographic separation to produce L-xylose and D-arabinose fractions.

The separation was performed in a chromatographic column (diameter 0.1 m) as a batch process. A strongly acid cation exchange resin in Na$^+$ form was used, the bed height was about 1.5 m. The cross linkage degree of the resin was 5.5% and the average particle size 0.3 mm. A feed size of about 250 g dry substance was used having a concentration of 35 g/100 ml. The separation temperature was 65° C. and flow rate 50 ml/min. The separation was performed as follows:

Step 1.

About 700 ml of filtered feed solution was introduced to the top of the resin bed.

Step 2.

The feed solution was eluted downwards in the column by feeding ion exchanged water to the top of the resin bed.

Step 3.

The outflow of the column was monitored continuously by on-line dry substance (refractive index) and conductivity measurement device. The outflow was collected in separate tubes in 2 min. intervals.

Step 4.

The composition of the collected samples was analyzed with HPLC (Pb$^{++}$ resin) and a capacity calculation of the two product fractions made.

Table 2 presents the composition of the feed solution and the out-flow fraction. The yield is calculated by dividing the amount of L-xylose of the product fraction by the amount of L-xylose of all outcoming fractions.

TABLE 2

Composition of feed solution and outflow fractions

| | Vol, I | DS, g/100 g | L-xylose, % on DS | D-arabinose, % on DS | L-xylose yield, % | D-arabinose yield, % |
|---|---|---|---|---|---|---|
| Feed solution | 0.7 | 30.0 | 30 | 30 | — | — |
| Residual fraction | 2.5 | 4.0 | 4.0 | — | 5 | 0 |
| L-xylose fraction | 1.9 | 4.5 | 65 | 18 | 85 | 20 |
| D-arabinose fraction | 1.6 | 4.0 | 15 | 60 | 10 | 80 |

EXAMPLE 16

Crystallization of L-xylose and Chiral Purity of the Product

The crystallization feed syrup (966 g, RDS 6.2, pH 5.2, purity 62.8% on DS) was prepared by chromatographic separation of a decarboxylation reaction mixture similarly as described in example 14. In addition to L-xylose, the feed syrup was analyzed to contain glycerol, erythritol, arabitol, xylitol, sorbitol, arabinose and lyxose. The crystallization was made by using a Buchi Rotavapor RE120 rotating evaporator. The feed syrup sample was taken after 2 hours concentration at 40 mbar vacuum (229 g syrup, RDS 25.8) and evaporation was continued 1.5 hours. The syrup (62 g, RDS 86.8%, 53.8 g DS) was seeded at 63° C. with 0.003 g L-xylose crystals (Fluka 95720, crystal size about 0.03 mm) and cooled stepwise to 41.5° C. during 25 hours. The crystals were separated from the mother liquid by using a Hettich Rotina 48 RSC laboratory basket centrifuge (5 min, 3500 rpm, 20 cm diameter, 0.15 filtering screen) without washing. The overall yield was 16.73 g centrifuged crystals and 25.13 g mother liquid. Dry crystal yield was 16.38 g after 1.5 h at 60° C. and 1 atm. The analyses made are presented in table 3.

TABLE 3

Purity of L-xylose

| Analysis/Sample | Feed syrup | Mother liquid | Dried crystals |
|---|---|---|---|
| RDS, % | 25.8 | 83.7 | — |
| DS (K-F), % | 25.5 | 83.5 | 99.64 |
| Purity, % on DS | 62.8 | 38.7 | 92.0 |

RDS = Refractometric dry substance content by using D-xylose RI/DS correlation, %
DS = Dry substance content analyzed by Karl-Fisher titration, % w/w
Purity = Xylose content analyzed by HPLC, resins in Pb$^{2+}$ form, % on DS The melting point of the dried crystals was 135.6° C. The crystallization yield was 66.4% of L-xylose.

The L-xylose crystals from the 1$^{st}$ crystallization step (16 g, xylose content 92% on DS, pure L-xylose, containing less than 0.3% D-form; detection limit for gas chromatography) were dissolved in water and the resulting 50% w/w liquid was purified with active carbon and filtrated. The purified liquid was evaporated, seeded with the L-xylose seed crystals and crystallized by evaporation and cooling between 20° C. and 70° C. The resulting crystals were separated from the mother liquid by centrifuging, in a laboratory basket centrifuge, and washing (about 10% water of the crystals). The xylose yield was about 60% of xylose. The crystals were dried and analysed as follows:

| | |
|---|---|
| water content | less than 0.5% |
| xylose purity | 98–102% on DS (HPLC, resins in Pb$^{2+}$ form) |
| chiral purity | >99.7% L-xylose (gas chromatography detection limit) |
| melting point | 150–153° C. |

Another purification method that can be used is affination with water or an organic solvent like ethanol.

EXAMPLE 17

Purity of L-xylose

Crystallization of L-xylose was made similarly as described in example 16. The melting point was measured visually by using the EurPh method, the sample was grounded and dried, the analysis speed was 2C/min. Table 4 presents the results from three samples.

TABLE 4

Purity and melting point of L-xylose crystals

| | Batch | Batch | Batch |
|---|---|---|---|
| FeedQ | 94.4 | 95.5 | 93.1 |
| Crystal analysis: | | | |
| Borate, HPLC % | 0.05 | 0.10 | 0.16 |
| Boron ppm | 62 | 43 | 4 |
| humidity % | 0.09 | 0.08 | 0.11 |
| purity % | 100 | 100 | 99.9 |
| mp, mean ° C. | 153.9 | 153.5 | 153.6 |
| mp, min. | 153.6 | 153.4 | 153.5 |
| mp, max. | 154.1 | 153.6 | 153.8 |
| DSC peak 10 C/min | 154.6 | 155.5 | 155.3 |

EXAMPLE 18

Reduction of L-xylose to Xylitol by Hydrogenation

Purified L-xylose, having a purity of 99% DS, was hydrogenated to xylitol in the following circumstances. Feed syrup dry substance was 50 g/100 ml, and temperature was 100° C. Raney-nickel was used as a catalyst and the catalyst load was 10% wet catalyst per total feed dry substance. Hydrogen pressure was 40 bar. The purity of xylitol after 3 hours hydrogenation was 98.5% on DS.

EXAMPLE 19

Crystallization of Xylitol

The crystallization feed syrup (2000 ml, DS concentration on 45 g/100 ml, xylitol purity 98.7% on DS) was prepared by hydrogenation of purified L-xylose in a similar manner as described in example 18. The feed syrup was evaporated, seeded with xylitol seed crystals (0.05 mm crystal size) and crystallized by evaporation and cooling between 40° C. and 65° C. The resulting crystals were separated from the mother liquid by centrifuging and washing (about 5% water of the crystals). The crystal yield was about 62% of xylitol. The crystals were dried and analysed as follows:

water content less than 0.2% xylitol purity 99.5% on DS (HPLC, resins in $Pb^{2+}$ form)

What is claimed is:

1. A process for the preparation of xylitol, the process comprising:
   (a) preparing L-xylose from a 6-carbon monosaccharide or a hydroxy acid derivative thereof by reduction and decarboxylation;
   (b) purifying the L-xylose prepared in step (a); and
   (c) reducing the purified L-xylose to xylitol;
wherein the 6-carbon monosaccharide or hydroxy acid derivative thereof is L-gulonic acid which is partly or totally present in epimer form as L-idonic acid.

2. The process according to claim 1, wherein L-idonic acid is prepared by fermentation.

3. The process according to claim 2, wherein L-idonic acid is prepared by fermentation of D-glucose.

4. The process according to claim 2, wherein L-idonic acid is prepared by fermentation of L-sorbose.

5. The process according to claim 2, wherein L-idonic acid is prepared by fermentation of D-sorbitol.

6. The process according to claim 2, wherein L-idonic acid is prepared by fermentation of 5-keto-D-gluconic acid.

7. The process according to claim 1, wherein the L-idonic acid is prepared by reduction of 5-keto-D-gluconic acid.

8. A the process for the preparation of xylitol, the process comprising:
   (a) preparing L-xylose from a 6-carbon monosaccharide or a hydroxy acid derivative thereof by reduction and decarboxylation;
   (b) purifying the L-xylose prepared in step (a); and
   (c) reducing the purified L-xylose to xylitol;
wherein L-xylonic acid is an intermediate.

9. The process according to claim 8, wherein said L-xylonic acid is prepared by decarboxylation of 2-keto-L-gulonic acid or L-sorbose, and subsequently said L-xylonic acid is reduced to L-xylose.

10. A process for the preparation of xylitol, the process comprising:
    (a) preparing L-xylose from a 6-carbon monosaccharide or a hydroxy acid derivative thereof by reduction and decarboxylation;
    (b) purifying the L-xylose prepared in step (a); and
    (c) reducing the purified L-xylose to xylitol;
wherein L-xylulose is an intermediate.

11. The process according to claim 10, wherein said L-xylulose is produced by decarboxylation of 2-keto-L-gulonic acid, and then isomerized to L-xylose.

12. The process according to claim 10, wherein said L-xylulose is prepared by oxidation of xylitol and then isomerized to L-xylose.

13. A the process for the preparation of xylitol, the process comprising:
    (a) preparing L-xylose from a 6-carbon monosaccharide or a hydroxy acid derivative thereof by reduction and decarboxylation;
    (b) purifying the L-xylose prepared in step (a); and
    (c) reducing the purified L-xylose to xylitol
wherein the purity of the L-xylose is about 98.5% or more and the melting point is over 153° C.

14. A process for the preparation of xylitol, the process comprising:
    (a) preparing L-xylose from a 6-carbon monosaccharide or a hydroxy acid derivative thereof by reduction and decarboxylation;
    (b) purifying the L-xylose prepared in step (a); and
    (c) reducing the purified L-xylose to xylitol
wherein the chiral purity of crystalline L-xylose is over 99.7%.

* * * * *